(12) United States Patent
Summar et al.

(10) Patent No.: US 12,329,732 B2
(45) Date of Patent: Jun. 17, 2025

(54) CITRULLINE FOR TREATMENT OF SICKLE CELL CRISIS

(71) Applicant: Vanderbilt University, Nashville, TN (US)

(72) Inventors: Marshall L. Summar, Washington, DC (US); Frederick E. Barr, Little Rock, AR (US); Suvankar Majumdar, Rockville, MD (US)

(73) Assignees: Vanderbilt University, Nashville, TN (US); The University of Mississippi Medical Center, Jackson, MS (US)

( * ) Notice: Subject to any disclaimer, the term of this patent is extended or adjusted under 35 U.S.C. 154(b) by 278 days.

(21) Appl. No.: 17/832,058

(22) Filed: Jun. 3, 2022

(65) Prior Publication Data

US 2022/0304966 A1    Sep. 29, 2022

Related U.S. Application Data

(63) Continuation of application No. 15/906,852, filed on Feb. 27, 2018, now Pat. No. 11,351,135.

(60) Provisional application No. 62/463,931, filed on Feb. 27, 2017.

(51) Int. Cl.
*A61K 31/198*  (2006.01)
*A61K 9/00*    (2006.01)
*A61P 7/06*    (2006.01)

(52) U.S. Cl.
CPC .......... *A61K 31/198* (2013.01); *A61K 9/0019* (2013.01); *A61K 9/0073* (2013.01); *A61P 7/06* (2018.01)

(58) Field of Classification Search
CPC ........ A61K 31/198; A61K 9/0019; A61P 7/06
See application file for complete search history.

(56) References Cited

U.S. PATENT DOCUMENTS

| | | |
|---|---|---|
| 6,028,107 A | 2/2000 | Waugh |
| 8,536,225 B2 | 9/2013 | Summar et al. |
| 9,375,451 B2 | 6/2016 | Hibbert et al. |
| 2009/0312423 A1 | 12/2009 | Summar et al. |
| 2012/0076859 A1 | 3/2012 | Hoffman |
| 2016/0296586 A1 | 10/2016 | Morita et al. |
| 2016/0374972 A1 | 12/2016 | Summar et al. |

FOREIGN PATENT DOCUMENTS

| | | | |
|---|---|---|---|
| GB | 2322551 A | | 9/1998 |
| WO | WO 00/21543 | * | 4/2000 |

OTHER PUBLICATIONS

Majumdar et al. (2018) British Journal of Haematology [epub] 3 pages.
Smith et al., Nitric oxide precursors and congenital heart surgery: A randomized controlled trial of oral citrulline, Journal of Thoracic and Cardiovascular Surgery, 2006, 132 ( 1 ): 58-65.
Barr et al., Pharmacokinetics and safety of intravenously administered citrulline in children undergoing congenital heart 2 surgery: Potential therapy for postoperative pulmonary hypertension, Journal of Thoracic and Cardiovascular Surgery, 2007, 134 (2): 319-326.

* cited by examiner

*Primary Examiner* — Sahar Javanmard
(74) *Attorney, Agent, or Firm* — ArentFox Schiff LLP (57) ABSTRACT

A method for administration of citrulline for the treatment of sickle cell disease and other complications of sickle cell disease thereof.

19 Claims, 4 Drawing Sheets

CITRULLINE FOR TREATMENT OF SICKLE CELL CRISIS

CROSS-REFERENCE TO RELATED APPLICATIONS

This patent application is a continuation application of U.S. patent application Ser. No. 15/906,852, filed Feb. 27, 2018, which claims the benefit of priority to U.S. Provisional Patent Application No. 62/463,931, filed Jun. Feb. 27, 2017, the contents of each of which are hereby incorporated by reference in their entireties.

FIELD OF THE INVENTION

The present invention relates generally to the field of treating patients with sickle cell disease and sickle cell crisis by administration of citrulline.

BACKGROUND OF THE INVENTION

Nitric Oxide

Nitric Oxide, a potent vasodilator, is produced by vascular endothelial cells in response to many different stimuli. Nitric oxide diffuses from the vascular endothelial cell to the vascular smooth muscle cell where it activates guanylate cyclase, leading to increased intracellular levels of cyclic GMP (cGMP). Increased cGMP, in turn, leads to relaxation of the vascular smooth muscle cell and increased blood flow. The extremely short half-life of NO allows for very tight vasoregulation.

Nitric oxide is synthesized by different isoforms of the enzyme nitric oxide synthase (NOS). Endothelial NOS (eNOS) is a constitutive enzyme responsible for the calcium-calmodulin dependent production of baseline levels of NO. Inducible NOS (iNOS) catalyzes the calcium-independent production of large amounts of NO in response to certain cytokines and inflammatory stimuli. A third form of NOS is neuronal NOS (nNOS) serves as a neurotransmitter in both the central and peripheral nervous systems. Endothelial cells generate endogenous NO from arginine. Palmer et al. *Biochem Biophys Res Commun* (1988) 153: 1251-6; Moncada et al. *N Engl J Med* (1993) 329: 2002-12. In fact, two urea cycle enzymes, argininosuccinic acid synthetase (ASS) and argininosuccinic acid lyase (ASL), participate in the NO regeneration pathway in endothelial tissues (FIG. 1).

As part of work on defective waste nitrogen processing, it has been found that the hepatic urea cycle has a very important role in the production of two precursors of nitric oxide, namely arginine and citrulline. Arginine is a basic amino acid synthesized predominantly by the urea cycle (FIG. 1). Citrulline is a naturally occurring amino acid and the first intermediate in the urea cycle (FIG. 1) as well as a precursor to arginine and nitric oxide (NO). The first two steps of the hepatic urea cycle, carried out by carbamyl phosphate synthetase I(CPSI) and ornithine transcarbamylase (OTC), are limited to the mitochondria in the liver and gut, with the remainder of the pathway distributed throughout the body, including the pulmonary vascular endothelium. Summar (1998) *Journal of Inherited Metabolic Disease* 21(S1): 30-39.

In the next urea cycle step, citrulline is transported from the mitochondria to the cytoplasm. After citrulline is transported intracellularly via a selective membrane transporter, it is rapidly converted to arginine by the enzymes argininosuccinate synthetase (AS) and argininosuccinate lyase (AL). Argininosuccinate synthetase (AS) is the first of the cytoplasmic urea cycle enzymes and combines citrulline with aspartate to form argininosuccinate. See FIG. 1. Argininosuccinate lyase (AL) cleaves fumarate off of argininosuccinate to form arginine. See FIG. 1.

Citrulline and the Urea Cycle

The new substrate supply for the NO pathway comes entirely from the production of citrulline as part of normal urea cycle function. Therefore, a theoretical link exists between NO production and urea cycle function. Intracellular concentrations of arginine are many times greater that circulating plasma concentrations, yet NOS function appears to be regulated by plasma concentrations of arginine. Current theory proposes that this phenomenon is due to intracellular co-localization of the arginine transporter, CAT-1, and eNOS in the plasma membrane. CAT-1 uptake of plasma arginine is directly channeled into NO synthesis via eNOS while intracellular arginine stores are separately compartmentalized and unavailable. Both arginine and citrulline can be given orally, however the gut has a partially intact urea cycle and arginase converts much of the dietary arginine to urea. In normal volunteers, oral L-citrulline increases circulating arginine concentrations more than oral arginine. Consequently, systemic citrulline provides a much more reliable mode of generating NO in tissue.

Sickle Cell Disease

Sickle cell disease (SCD) is a group of genetically transmitted blood disorders. The most common type is known as sickle cell anemia (SCA). It results in an abnormality in the oxygen-carrying protein hemoglobin found in red blood cells. This leads to a rigid, sickle-like shape under certain circumstances. A number of health problems may develop, around 5 to 6 months of age, such as attacks of pain ("sickle cell crisis"), anemia, bacterial infections, and stroke. Long term pain may develop as a patient ages. The average life expectancy of a patient with SCD in the developed world is 40 to 60 years. "Sickle Cell Disease" National Heart, Lung, and Blood Institute website (2016).

Sickle cell disease is genetic and is caused when a patient is homogeneous abnormal hemoglobin gene. National Heart, Lung, and Blood Institute (2016). Several subtypes exist, depending on the exact mutation in each hemoglobin gene. A SCD attack can be set off by temperature changes, stress, dehydration, and high altitude. A person with a single abnormal copy does not usually have symptoms and is said to have sickle cell trait. Diagnosis is by a blood test, and some countries test all babies at birth for the disease. Diagnosis is also possible during pregnancy. "Sickle Cell Disease" National Heart, Lung, and Blood Institute website (2016)

Treatment of patients with sickle cell disease may include infection prevention with vaccination and antibiotics, high fluid intake, folic acid supplementation, and pain medication. Other measures may include blood transfusion, and the medication hydroxycarbamide (hydroxyurea). A small proportion of people can be cured by a transplant of bone marrow cells. "Sickle Cell Disease" National Heart, Lung, and Blood Institute website (2016).

As of 2013 about 3.2 million people have sickle cell disease while an additional 43 million have sickle cell trait. *Global Burden of Disease Study* 2013 Collaborators (2015) Lancet 386. About 80% of sickle cell disease cases are believed to occur in sub-Saharan Africa. Rees et al. (2010)

*Lancet* 376(9757): 2018-31. It also occurs relatively frequently in parts of India, the Arabian peninsula, and among people of African origin living in other parts of the world. Elzouki & Abdelaziz (2012). *Textbook of clinical pediatrics* ($2^{nd}$ Ed.). Berlin: Springer page 2950. In 2013, it resulted in 176,000 deaths, up from 113,000 deaths in 1990. GBD 2013 Mortality and Causes of Death, Collaborators (17 Dec. 2014). "Global, regional, and national age-sex specific all-cause and cause-specific mortality for 240 causes of death, 1990-2013: a systematic analysis for the Global Burden of Disease Study 2013.". Lancet 385: 117-171. The condition was first described in the medical literature by the American physician James B. Herrick in 1910. Savitt & Goldberg (1989) *JAMA* 261(2): 266-71; Serjeant (2010) *British Journal of Haematology* 151(5): 425-9. Sickle cell disease may lead to various acute and chronic complications, several of which have a high mortality rate. Yawn et al. (2014) *JAMA* 312(10): 1033-48.

Bone marrow transplant offers the only potential cure currently available for sickle cell anemia. But finding a donor is difficult and the procedure has serious risks associated with it, including death. As a result, treatment for sickle cell anemia is usually aimed at avoiding crises, relieving symptoms and preventing complications. Mayo Clinic Website "Sickle Cell Anemia—Treatments and Drugs" (2016). Thus, there exists a need in the art for improved treatment of sickle cell anemia and sickle cell crisis.

SUMMARY OF VARIOUS EMBODIMENTS OF THE INVENTION

This invention provides a method for treating sickle cell disease in a patient comprising administering a composition comprising an effective amount of citrulline to the patient in need thereof. Additionally this invention provides a method for treating sickle cell anemia in a patient comprising administering a composition comprising an effective amount of citrulline to the patient in need thereof. Alternatively, this invention provides a method of treating a complication of sickle cell crisis in a patient comprising administering a composition comprising an effective amount of citrulline to a patient in need thereof, where the complication may be sickle cell crisis, vaso-occlusive crisis, acute chest syndrome, aplastic crisis, hemolytic crisis, dactylitis, acute chest syndrome, seizure, stroke, ischemia, transient ischemic attack, ischemic colitis, or a combination thereof. The effective amount of citrulline may be 100-1,000 mg/kg; in particular the effective amount of citrulline may be 100, 200, 300, 400, 500, 600, 700, 800, 900, or 1,000 mg/kg, and the citrulline may be provided in dose unit form. According to this invention, citrulline may be administered orally, intravenously, or a combination thereof.

In particular embodiments, the patient having sickle cell disease, including sickle cell anemia, are also hypocitrullinemic, and the effective amount of citrulline will raise the patient's plasma citrulline level above 37 µmol/L upon administration, more preferably the patient's plasma citrulline level is raised above 100 µmol/L; even more preferably, the patient's plasma citrulline level is raised to about 100-200 µmol/L, and/or the patient's plasma citrulline level is raised for up to 48 hours.

In the embodiments of this invention, the typical patient is a mammal, and the mammal may be human. Patients according to this invention may be less than about 6 years old, or the patient may be less than about 10 days old. Further, patients may be a child, juvenile, or adult.

In particular embodiments of this invention, the patient is at risk for acute lung injury.

In the embodiments of this invention, a method of treating or preventing a complication of sickle cell disease in a patient may comprise administering a composition to a patient in need thereof comprising an effective amount of citrulline effective to mitigate the complication. The complication may be sickle cell crisis, vaso-occlusive crisis, acute chest syndrome, aplastic crisis, hemolytic crisis, dactylitis, acute chest syndrome, seizure, stroke, ischemia, transient ischemic attack, ischemic colitis, or a combination thereof. The complication may be sickle cell crisis.

In the embodiments of this invention, a method for treating sickle cell anemia in a patient may comprise administering a composition comprising an effective amount of citrulline to the patient in need thereof.

In the embodiments of this invention, the effective amount of citrulline may be 100-1,000 mg/kg. The effective amount of citrulline may be 100, 200, 300, 400, 500, 600, 700, 800, 900, or 1,000 mg/kg. The effective amount of citrulline may be 100-1,000 mg in dose unit form. The effective amount of citrulline may be 100, 200, 300, 400, 500, 600, 700, 800, 900, or 1,000 mg in dose unit form.

In the embodiments of this invention, the method may comprise an initial bolus of citrulline at 10-30 mg/kg of citrulline over five minutes and, one hour after the administration of the bolus, a continuous infusion of citrulline at 1-10 mg/kg/hour for 1-24 hours.

The method may comprise an intravenous bolus of 5-50 mg/kg of citrulline. The intravenous bolus may comprise about 5, 6, 7, 8, 9, 10, 15, 20, 21, 22, 23, 24, 25, 30, 35, 40, 45, or 50 mg/kg of citrulline. The intravenous bolus may comprise about 5-10, 15-25, or 30-50 mg/kg of citrulline.

In the embodiments of this invention, the method may comprise an intravenous bolus of 20 mg/kg of citrulline over 1-60 minutes. The method may comprise an intravenous bolus of 20 mg/kg of citrulline over 1 minute, 2, 3, 4, 5, 6, 7, 8, 9, 10, 11, 12, 15, 20, 25, 30, 35, 40, 45, 50, 55, or 60 minutes. The method may comprise an intravenous bolus of 20 mg/kg of citrulline over 1-5 minutes, 6-10, 11-15, 20-25, 30-35, 40-45, or 50-60 minutes. The method may further comprise a second an intravenous bolus of 5-50 mg/kg of citrulline over 1-10 minutes.

In the embodiments of this invention, the method may further comprise a second an intravenous bolus of 5-50 mg/kg of citrulline over 1-10 minutes an hour after the first intravenous bolus of citrulline.

In the embodiments of this invention, the method may comprise an intravenous bolus of 20 mg/kg of citrulline over five minutes with dose increments of 10 mg/kg until a target plasma citrulline level of 80 to 100 µmol/L is reached.

The method may comprise a continuous infusion of citrulline at 1-10 mg/kg/hour. The continuous infusion of citrulline may be at about 1, 2, 3, 4, 5, 6, 7, 8, 9, or 10 mg/kg/hour. The continuous infusion of citrulline is may be at about 1-5, 6-9, or 8-10 mg/kg/hour.

In many embodiments, the continuous infusion may be for 1-24 hours. The continues infusion may be for about 1, 2, 3, 4, 5, 6, 7, 8, 9, 10, 11, 12, 13, 14, 15, 16, 17, 18, 19, 20, 21, 22, 23, or 24 hours.

In many embodiments, the patient's plasma citrulline level may be raised above 37 µmol/L. The patient's plasma citrulline level may be raised above 40 µmol/L, 50 µmol/L, 60 µmol/L, 70 µmol/L, 80 µmol/L, 90 µmol/L, 100 µmol/L, 110 µmol/L, 120 µmol/L, 130 µmol/L, 140 µmol/L, 150 µmol/L, 160 µmol/L, 170 µmol/L, 180 µmol/L, 190 µmol/L, or 200 µmol/L. The patient's plasma citrulline level may be raised to about 50-100 μmol/L, 75-100 μmol/L, 80-100 μmol/L, or 90-100 μmol/L. The patient's plasma citrulline level may be raised above 100 μmol/L. The patient's plasma citrulline level may be raised to about 100-200 μmol/L.

In many embodiments, the patient's plasma citrulline level may be raised for up to 48 hours. The patient's plasma citrulline level may be raised for at least 24 hours. The patient's plasma citrulline level is raised for at least 48 hours. The patient's plasma citrulline level may be raised above 50-100 μmol/L within 2 hours, 5 hours, 10 hours, 12, hours, 14, hours, 16 hours, 18 hours, 20 hours, 24 hours, 36 hours, or 48 hours.

In many embodiments, the patient may be at risk for acute lung injury.

In many embodiments, the patient may have a T1405N genotype in the CPSI gene of CC, AC, AA, or a combination thereof. The patient may have a T1405N genotype in the CPSI gene of CC.

In the embodiments of this invention, the effective amount of citrulline is an amount sufficient to prevent or reduce uncoupling of the eNOS dimer.

In the embodiments of this invention, the patient may have relative hypocitrullinemia. The patient with relative hypocitrullinemia may have a plasma citrulline level below 40, 50, 60, 70, 80, 90, or 100 μmol/L citrulline. The patient's plasma citrulline level may be below 80-100 μmol/L citrulline.

Citrulline according to this invention may be formulated for oral administration, inhalation administration, or intravenous administration.

This invention also provides pharmaceutical compositions comprising citrulline for the treatment of a complication of sickle cell anemia, where the complication may be sickle cell crisis, vaso-occlusive crisis, acute chest syndrome, aplastic crisis, hemolytic crisis, dactylitis, acute chest syndrome, seizure, stroke, ischemia, transient ischemic attack, ischemic colitis, or a combination thereof. Compositions according to this invention may be formulated for oral administration or intravenous administration.

This invention also provides pharmaceutical compositions comprising citrulline for the treatment or prevention of a complication of sickle cell disease, where the complication may be sickle cell crisis, vaso-occlusive crisis, acute chest syndrome, aplastic crisis, hemolytic crisis, dactylitis, acute chest syndrome, seizure, stroke, ischemia, transient ischemic attack, ischemic colitis, or a combination thereof.

In many embodiments, the effective amount of citrulline for pharmaceutical compositions of the invention may be 100-1,000 mg/kg. The effective amount of citrulline may be 100, 200, 300, 400, 500, 600, 700, 800, 900, or 1,000 mg/kg. The effective amount of citrulline may be 100-1,000 mg in dose unit form. The effective amount of citrulline may be 100, 200, 300, 400, 500, 600, 700, 800, 900, or 1,000 mg in dose unit form.

Compositions according to this invention may be formulated for oral administration, inhalation administration, or intravenous administration.

DETAILED DESCRIPTION OF PREFERRED EMBODIMENTS

The invention provides for a method by administration of citrulline, preferably via intravenous administration of citrulline, for the treatment of sickle cell anemia and complications thereof. In another mode, this invention provides for a method by administration of citrulline, preferably via intravenous administration of citrulline, for the treatment of sickle cell disease and complications thereof. In a preferred mode, citrulline is administered to a patient suffering from sickle cell crisis; more preferably, the patient to be treated is also exhibiting relative hypocitrullinemia.

In order that the invention herein described may be fully understood, the following detailed description is set forth. Various embodiments of the invention are described in detail and may be further illustrated by the provided examples. Additional viable variations of the embodiments can easily be envisioned.

Sickle Cell Disease Complications—Sickle Cell Crisis

The terms "sickle cell crisis" or "sickling crisis" may be used to describe several independent acute conditions occurring in patients with sickle cell disease (SCD). SCD results in anemia and crises that could be of many types including the vaso-occlusive crisis, aplastic crisis, sequestration crisis, hemolytic crisis, and others. Most episodes of sickle cell crises last between five and seven days. Although infection, dehydration, and acidosis (all of which favor sickling) can act as triggers, in most instances, no predisposing cause is identified. Kumar et al. (2009) Robbins and Cotran Pathologic Basis of Disease, Professional Edition: Expert Consult—Online (Robbins Pathology) Elsevier Health. Kindle Edition. Preferred modes of this invention include administration of citrulline to patients with SCD who are in one or another form of sickle cell crisis or who have been exposed to a predisposing cause or trigger for sickle cell crisis.

The present invention provides for spray dry preparations comprising citrulline for the treatment of sickle cell disease (SCD), preferably a complication of sickle cell anemia, including but not limited to sickle cell crisis, vaso-occlusive crisis, aplastic crisis, hemolytic crisis, dactylitis, acute chest syndrome, seizure, stroke, ischemia, transient ischemic attack, ischemic colitis, or a combination thereof.

Vaso-Occlusive Crisis

The vaso-occlusive crisis is caused by sickle-shaped red blood cells that obstruct capillaries and restrict blood flow to an organ resulting in ischemia, pain, necrosis, and often organ damage. The frequency, severity, and duration of these crises vary considerably. Painful crises are treated with hydration, analgesics, and blood transfusion; pain management requires opioid administration at regular intervals until the crisis has settled. For milder crises, a subgroup of patients manage on NSAIDs (such as diclofenac or naproxen). For more severe crises, most patients require inpatient management for intravenous opioids; patient-controlled analgesia devices are commonly used in this setting. Vaso-occlusive crisis involving organs such as the penis, or lungs are considered an emergency and treated with red-blood cell transfusions. Incentive spirometry, a technique to encourage deep breathing to minimize the development of atelectasis, is recommended. Glassberg (2011) *Emergency Medicine Practice* 13 (8): 1-20; Olujohungbe & Burnett (2013) *British Journal of Haematology* 160(6): 754-65.

Splenic Sequestration Crisis

Because of its narrow vessels and function in clearing defective red blood cells, the spleen is frequently affected. Anie K A, Green J (2012). Anie, Ed. "Psychological therapies for sickle cell disease and pain". Cochrane Database of Systematic Reviews 2: CD001916. It is usually infarcted before the end of childhood in individuals suffering from sickle cell anemia. This spleen damage increases the risk of infection from encapsulated organisms; Pearson (1977) *J Infect Dis.* 136 Suppl: S25-30; Wong et al. (1992) *Am J Hematol* 39 (3): 176-82; preventive antibiotics and vaccinations are recommended for those lacking proper spleen function.

Splenic sequestration crises are acute, painful enlargements of the spleen, caused by intrasplenic trapping of red cells and resulting in a precipitous fall in hemoglobin levels with the potential for hypovolemic shock. Sequestration crises are considered an emergency. If not treated, patients may die within 1-2 hours due to circulatory failure. Management is supportive, sometimes with blood transfusion. These crises are transient, they typically continue for 3-4 hours and may last for as long as a day. Khatib et al. (2009) *Pediatric Radiology* 39(1): 17-22.

Acute Chest Syndrome

Acute chest syndrome (ACS) is defined by at least two of the following signs or symptoms: chest pain, fever, pulmonary infiltrate or focal abnormality, respiratory symptoms, or hypoxemia. Glassberg (2011) *Emergency Medicine Practice* 13(8): 1-20. It is the second-most common complication and it accounts for about 25% of deaths in patients with SCD, majority of cases present with vaso-occlusive crises when they develop ACS. Mekontso et al. (2008) *Am. J. Respir. Crit. Care Med.* 177(6): 646-53; Paul et al. (2011) *Eur. J. Haematol.* 87(3): 191-207. Nevertheless, about 80% of patients have vaso-occlusive crises during ACS.

Aplastic Crisis

Aplastic crises are acute worsening of the patient's baseline anemia, producing pale appearance, fast heart rate, and fatigue. This crisis is normally triggered by parvovirus B19, which directly affects production of red blood cells by invading the red cell precursors and multiplying in and destroying them. Kumar et al. (2009). Robbins and Cotran Pathologic Basis of Disease, Professional Edition: Expert Consult—Online (Robbins Pathology). Elsevier Health. Kindle Edition. Parvovirus infection almost completely prevents red blood cell production for two to three days. In normal individuals, this is of little consequence, but the shortened red cell life of SCD patients results in an abrupt, life-threatening situation. Reticulocyte counts drop dramatically during the disease (causing reticulocytopenia), and the rapid turnover of red cells leads to the drop in hemoglobin. This crisis takes 4 days to one week to disappear. Most patients can be managed supportively; some need blood transfusion. Slavov et al. (2011) *FEMS Immunology and Medical Microbiology* 62(3): 247-62.

Hemolytic Crisis

Haemolytic crises are acute accelerated drops in hemoglobin level. The red blood cells break down at a faster rate. This is particularly common in patients with coexistent G6PD deficiency. Balgir (2012) *Cardiovascular & Hematological Agents in Medicinal Chemistry* 10(1): 3-13. Management is supportive, sometimes with blood transfusions. Glassberg (2011) *Emergency Medicine Practice* 13(8): 1-20.

Other Complications of Sickle Cell Disease

One of the earliest clinical manifestations is dactylitis, presenting as early as six months of age, and may occur in children with sickle cell trait. Jadavji & Prober (1985) *Can Med Assoc J* 132 (7): 814-5. The crisis can last up to a month. Worrall & Butera (1976) *J Bone Joint Surg Am* 58 (8): 1161-3. Another recognized type of sickle crisis, acute chest syndrome, is characterized by fever, chest pain, difficulty breathing, and pulmonary infiltrate on a chest X-ray. Given that pneumonia and sickling in the lung can both produce these symptoms, the patient is treated for both conditions. Miller (2011) *Blood* 117 (20): 5297-305. It can be triggered by painful crisis, respiratory infection, bone-marrow embolization, or possibly by atelectasis, opiate administration, or surgery. Hematopoietic ulcers may also occur. James et al. (2006). Andrews' Diseases of the Skin: clinical Dermatology. Saunders Elsevier. page 847.

Mode of Action

Without being bound to a particular theory, the inventors point out that the pathophysiological hallmark of sickle cell disease (SCD) is vaso-occlusion in or of the small blood vessels. During times of deoxygenation, transformation and polymerization of hemoglobin S molecules occurs so that the doughnut shaped red blood cells (rbcs) assume a sickle shape resulting in a highly viscous and semi-solid gel that leads to microvascular obstruction (vaso-occlusion). Ferrone *Microcirculation* (2004) 11:115-128; Samuel et al. *Nature* 345: 833-835. Over the last several years it has become apparent that vaso-occlusion is a highly complex phenomenon with multiple factors that play important roles. Endothelial activation occurs as shown by increased expression of adhesion molecules and also increased expression of P-selectin by endothelial cells in mouse models of SCD. Solovey et al. *N Engl J Med* (1997) 337: 1584-1590. This promotes adhesion of deformed sickle red blood cells to the endothelium enabling further polymerization and trapping of sickle red-blood cells in the microcirculation with increased production of inflammatory cytokines. Hebbel et al. *N Engl J Med* (1980) 302: 992-995. Furthermore, endothelial activation propagates progressive recruitment and adhesion of leukocytes allowing greater interaction between sickle red-blood cells and white blood cells that further contributes to the process of vaso-occlusion. Finnegan et al. *Am J Hematol* (2007) 82: 266-275. Several studies have also shown that there is increased platelet activation and elevated markers of thrombosis indicating that SCD is a hypercoagulable state. Hsu et al. *Blood* (2007) 109: 3088-3098. In addition to the above factors, perturbations in the arginine pathway with hemolysis associated nitric oxide (NO) depletion have been found to play a central role in the pathogenesis of vaso-occlusion in SCD.

NO is a powerful vasodilator and plays a fundamental role in maintaining normal vasomotor tone. NO, a soluble gas continuously synthesized in endothelial cells by the NO synthase enzyme systems, regulates basal vascular tone and endothelial function. These vital homeostatic processes may be impaired in SCD and contribute to the pathogenesis of SCD complications such as Vaso-Occlusive crisis (VOC), leg ulcers and priapism due to disturbed NO production in the endothelium contributing to endothelial dysfunction and local vasoconstrictors exceeding vasodilators. Hence, NO plays a significant role in the pathophysiology of SCD.

NO is synthesized from arginine by a family of enzymes called the NO synthases (NOS). NOS catalyze the oxidation of arginine to NO and L-citrulline, and L-citrulline in turn can be recycled to arginine by the combined action of arginosuccinate synthase (ASS) and arginosuccinate lyase (ASL), which is expressed in all cell types. Arginine may also be catabolized by arginase to produce ornithine to fuel the urea cycle.

As a consequence of hemolysis and breakdown of the red blood cell membrane in SCD, reactive oxygen species are generated that may react with NO. During hemolysis, arginase from erythrocyte membranes is released into the circulation, and degrades Arginine, leading to further reduction in NO bioavailability. The limited intravascular hemolysis that occurs in SCD results in release of hemoglobin into plasma where it scavenges NO. Hsu et al. *Blood* (2007) 109: 3088-3098; Taylor et al. *PLos One* (2008) 3: e2095. Lactate dehydrogenase, a marker of intravascular hemolysis was found to be elevated in patients with SCD and is correlated with accelerated NO consumption. To different extents, all these factors contribute to the global depletion of NO associated with SCD.

Multiple studies have evaluated NO levels and precursors in SCD. Plasma arginine levels appear to vary with age and the presence of VOC. Morris et al. *J Pediatr Hematol Oncol* (2000) 22: 515-520. Arginine levels are normal in steady-state children with SCD, but significantly lower in children experiencing a VOC. Levels were normal at presentation of these patients, but decreased during hospitalization in those children with VOC, suggesting a relationship between the arginine-nitric oxide pathway and VOC in SCD. Adults with SCD have been shown to have low arginine levels during steady-state which significantly decreases further during a VOC. Oral arginine given to normal controls, SCD patients, and SCD patients hospitalized with a VOC increased NO formation by 68% in normal controls, whereas steady-state SCD patients demonstrated a paradoxical decrease in NO that was not overcome by higher doses, suggesting that arginine is metabolized differently in SCD than in healthy controls. In a randomized, double-blind placebo controlled clinical study the benefit of arginine in reducing parenteral opioid use in children with VOC and also lowered pain scores was demonstrated. Morris et al. *Haematologica* (2013) 98: 1375-1382. However, citrulline is a more potent NO booster than arginine for several reasons.

Arginine is subject to extensive elimination by arginases present both in the gut and liver. Morris *J Nutr* (2004) 134: 2743S-2747S; Morris *J Nutr* (2007) 137: 1602S-1609S. Arginine may act as a common substrate for both NOS and arginase, and arginase may reduce NO production by competing with NOS for arginine. Unlike arginine, citrulline is not subject to presystemic breakdown in the gut. The majority of citrulline released by the intestine is metabolized within the kidney where it is converted to arginine, known as the intestinal-renal axis, representing ~15% of de novo arginine production. Curis et al. *Amino Acids* (2005) 29: 177-205. Citrulline may therefore serve as an arginine precursor. As noted above, citrulline can also be converted to arginine via ASS and ASL. While both arginine and citrulline support NO synthesis in a variety of tissues, including the vascular endothelium, both NOS and arginase use arginine as a common substrate, and arginase may reduce NO production by competing with NOS for arginine, which makes citrulline a more effective NO precursor than arginine.

Endothelial cell activation plays a critical role in the vasculopathy associated with SCD. The significantly lower arginine levels during a VOC likely leads to an imbalance in the NO metabolism in the endothelium that contributes to the perfusion defects in the microvasculature in SCD. In an investigation in murine endothelial cells to determine whether arginosuccinate synthase, the rate limiting enzyme for arginine regeneration from citrulline, plays a pivotal role in supplying arginine to endothelial (eNOS), but not inducible (iNOS) for NO production, it was found that extracellular arginine was the only arginine supply for NO production by iNOS while due to the presence of arginosuccinate synthase in endothelial cells, citrulline was the major supply for intracellular arginine and endothelial NO production. Shen et al. *Biochem Pharmacol* (2005) 69: 97-104. The presence of arginosuccinate synthase in endothelial cells appears to play a critical role and offers the opportunity to use citrulline supplementation to increase intracellular endothelial arginine availability for NO product, which may be expected to help ameliorate the microcirculatory occlusion seen in SCD. Moreover, enhanced arginase-induced arginine consumption is believed to play an integral role in the pathogenesis of sickle cell complications, and in a more recent study, citrulline supplementation increased NO production and improved microcirculatory flow during conditions with acute arginase-induced arginine deficiency, while Arginine did not increase NO production. Wijands et al. *Nutrients* (2015) 7: 5217-5238.

Inhaled nitric oxide (iNO) has been shown to affect mouse models of sickle cell disease. However, a randomized, placebo-controlled study with iNO showed no effect on time-to-resolution of vaso-occlusive crisis. Gladwin et al. *JAMA* (2011) 305(9): 893-902. The present inventors speculate that the lack of effect in this study was due to the short half-life of NO in tissue generally and the short path length of diffusion for NO in lung tissue. On the other hand, endogenously-produced NO needs only to diffuse from vascular endothelial cells to nearby vascular smooth muscle cells.

A study giving citrulline orally twice daily in daily doses of approximately 0.1 g/kg in a pilot phase II clinical trial during steady states in four homozygous sickle cell disease subjects and one sickle cell hemoglobin C disease patient [ages 10-18] has been published. There was dramatic improvements in symptoms of well-being, raised plasma arginine levels, and reductions in high total leukocyte and high segmented neutrophil counts toward or to within normal limits. Continued citrulline supplementation in compliant subjects continued to lessen symptomatology, to maintain plasma arginine concentrations greater than control levels, and to maintain nearly normal total leukocyte and neutrophil counts. Side effects or toxicity from citrulline were not experienced. Waugh et al. *N Natl Med Assoc.* (2001) 93: 363-371.

Citrulline

Arginine is the substrate for nitric oxide production by nitric oxide synthetase. Because the majority of circulating arginine is from urea cycle synthesis and not dietary sources, citrulline availability is critical to maintaining adequate arginine supply for nitric oxide production. Citrulline is the first intermediate in the urea cycle after the rate-limiting enzyme carbamyl phosphate synthetase I. Citrulline also crosses mitochondrial and cellular membranes easily and therefore can be transported to other organs in the body. In the vascular endothelium (including the pulmonary endothelium), citrulline can then be converted into arginine and subsequently into nitric oxide. Consequently, modifying systemic citrulline to enhance endogenous NO production is a much more reliable method of delivering NO to tissue than iNO.

Oral administration of citrulline obligates the citrulline to pass through the gut and then the liver which removes the citrulline. This is due to the absorption of the citrulline from the gut and transport directly to the liver by the hepatic portal vein in the first pass through the patient's system. For example, the inventors found that only 2 out of 3 patients met the target level of citrulline when administered orally in an ICU(Intensive Care Unit). This would require multiple dosing regimen to achieve a therapeutic plasma level of citrulline. Thus, it is preferable for citrulline therapy to administer the active agent in a manner which bypasses the gut.

Relative Hypocitrullinemia

Relative hypocitrullinemia is a condition in which a subject suffering from the condition has reduced plasma citrulline as compared to a subject not suffering from the condition. Patients with relative hypocitrullinemia may have a plasma citrulline level below 100 μmol/L, for example below 37, 40, 50, 60, 70, 80, 90, or 100 μmol/L. For example, a patient with relative hypocitrullinemia may have a plasma citrulline level is below 80-100 μmol/L citrulline. These same patients do not suffer from statistically significant deficiencies in nitric oxide or arginine at a steady state. However, hypocitrullinemic patients may be much less responsive to a need for increased NO to stimulate vasodilation short term.

Methods of Use

Administration of citrulline results in an increase in plasma citrulline levels. Smith teaches that oral citrulline may be administered safely to increase and maintain plasma citrulline levels. Smith, et al. (2006) *J Thorac Cardiovasc Surg* 132: 58-65, FIG. 3. Barr teaches that intravenous citrulline may be administered safely to increase and maintain plasma citrulline levels. Barr, et al. (2007) *J Thorac Cardiovasc Surg* 134: 319-326, FIG. 5. Accordingly, the administration of citrulline may be used to overcome relative hypocitrullinemia by increasing the plasma citrulline levels.

Citrulline Formulations

Citrulline (2-amino-5-(carbamoylamino)pentanoic acid) [$C_6H_{13}N_3O_3$] is an amino acid. Citrulline solution for IV administration may be manufactured by methods known in the art. See, e.g., Kakimoto, et al. (1971) *Appl Microbiol* 22(6): 992-999.

The effective amount of citrulline may be about 100-300 μmol/L of plasma. The citrulline may be formulated to achieve a concentration of about 100, 125, 150, 175, 200, 225, 250, 275, or 300 μmol/L.

Citrulline Dosages

The citrulline may be provided in dose unit form. For example, the citrulline may be provided in a container containing 300 mg sterile citrulline formulated for injection. This may be reconstituted for use using 6 mL sterile water and further diluted with approximately 5.9 mL sterile NaCl solution 0.9% Ph. Eur. to a total volume of 12 mL and a concentration of 300 mg/12 mL (i.e., 25 mg/mL). The citrulline may be formulated for injection at a concentration of 10-40 mg/mL, for example 10, 15, 20, 25, 30, 35, or 40 mg/mL. The citrulline may be provided as a drug product at 500 mg sterile citrulline for injection in 10 mL of sterile water. This may be used to infuse patients using sodium chloride 0.9% Ph. Eur.

The effective amount of citrulline may be about 10-300 mg/kg. The effective amount of citrulline may be about 10, 25, 50, 75, 100, 125, 150, 175, 200, 225, 250, 275, or 300 mg/kg. In a preferred mode, the effective amount of citrulline may be about 150 mg/kg.

Alternatively, citrulline may be administered orally at a dosage of about 5-15 g/kg, i.e., about 5, 6, 7, 8, 9, 10, 11, 12, 13, 14, or 15 g/kg of citrulline. In a preferred mode, the oral dosage of citrulline may be about 9 g/kg of citrulline.

The target level for plasma citrulline may be maintained at about 37 μmol/L to 2.5 mM. For example, the plasma citrulline level of the patient may be maintained above 37, 40, 45, 50, 75, 100, 125, 150, 175, 200, 225, 250, or 300 μmol/L. The plasma citrulline level of the patient may be maintained above 37, 100, or 200 μmol/L. The methods described herein may be used to maintain a patient's citrulline plasma level between about 37 μmol/L to 200 μmol/L, 100 μmol/L to 1 mM/L, 150 μmol/L to 500 μmol/L citrulline. In a preferred mode, the plasma citrulline level may be maintained at about 100 μmol/L.

In some instances, it is desirable to deliver a unit dose, such as doses of 50 mg, more preferably 100 mg, and more preferably 160 mg of citrulline. The above described doses of 50 mg, 100 mg, 160 mg, 250 mg, and 300 mg may be delivered in a dose.

The following dose ranges relate to the goal of obtaining and maintaining a plasma citrulline level of 100 μM/L. The following dosing regimen may be used: an intravenous bolus dose of 20 mg/kg over 5 minutes and then continuous administration at a rate of 7 mg/kg/hour for the next 23 hours or an intravenous bolus does of 20 mg/kg followed by 9 mg/kg/hour for 23 hours or a lower continuous dose of 5 mg/kg/hour for 23 hours.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in surgery, biochemistry, medicine, physiology, and/or related fields are intended to be within the scope of the following claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The examples contained herein are offered by way of illustration and not by any way of limitation.

EXAMPLES

Example 1

Citrulline and Sickle Cell Crisis

Background: Hemolysis associated nitric oxide (NO) depletion plays a central role in the pathogenesis of vaso-occlusion in sickle cell disease (SCD). Citrulline is an effective NO booster, even during conditions of inflammation and acute arginase-induced arginine deficiency, characteristic of SCD. This study demonstrates the safety and pharmacokinetic profile of intravenous citrulline in patients with sickle cell disease and provides guidance for an appropriate dosage range.

Figure 1:
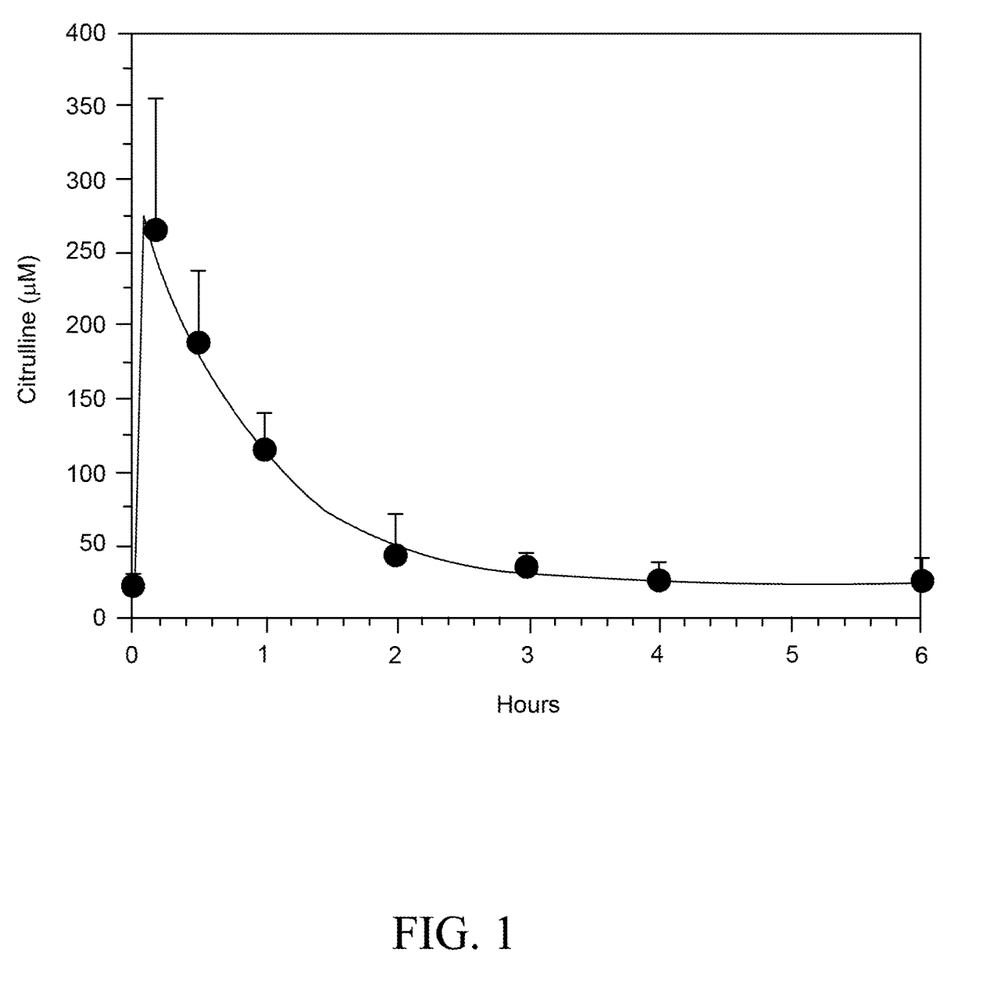
FIG. 1 depicts plasma citrulline levels in four patients over six hours after a 20 mg/kg intravenous bolus of citrulline within 5 minutes.

Methods: Each cohort of participants received an intravenous bolus of 20 mg/kg of citrulline over five minutes with dose increments of 10 mg/kg until a target plasma citrulline level of 80 to 100 µmol/L. FIG. 1. Plasma samples were collected at certain time points for pharmacokinetic studies. Adverse events were followed according to the NCI Common Terminology Criteria for Adverse Events (CTCAE).

Figure 2:
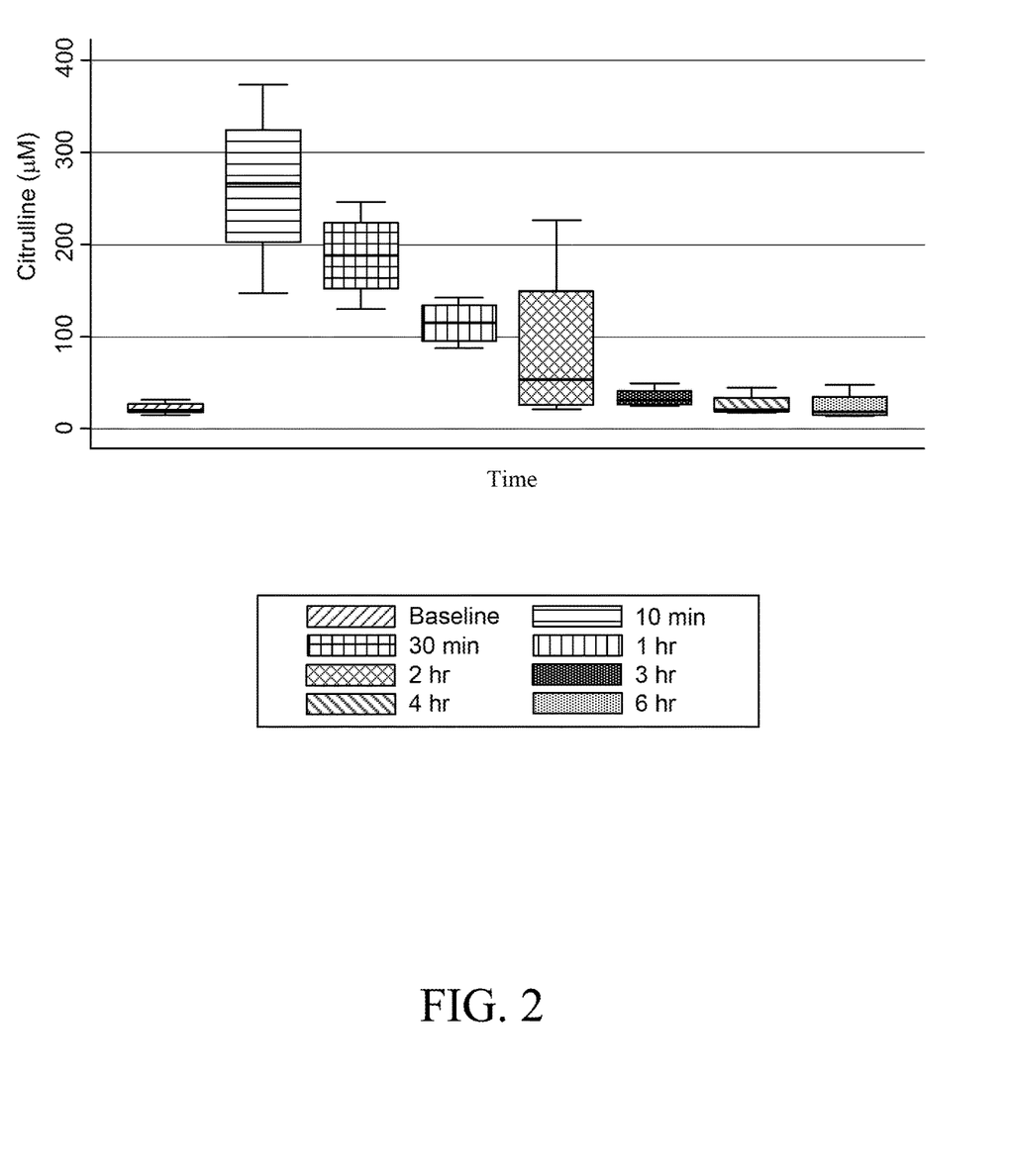
FIG. 2 depicts the variability of observed plasma citrulline levels in Patients 1-4 over 6 hours following a 20 mg/kg intravenous bolus of citrulline over 5 minutes.
Figure 3:
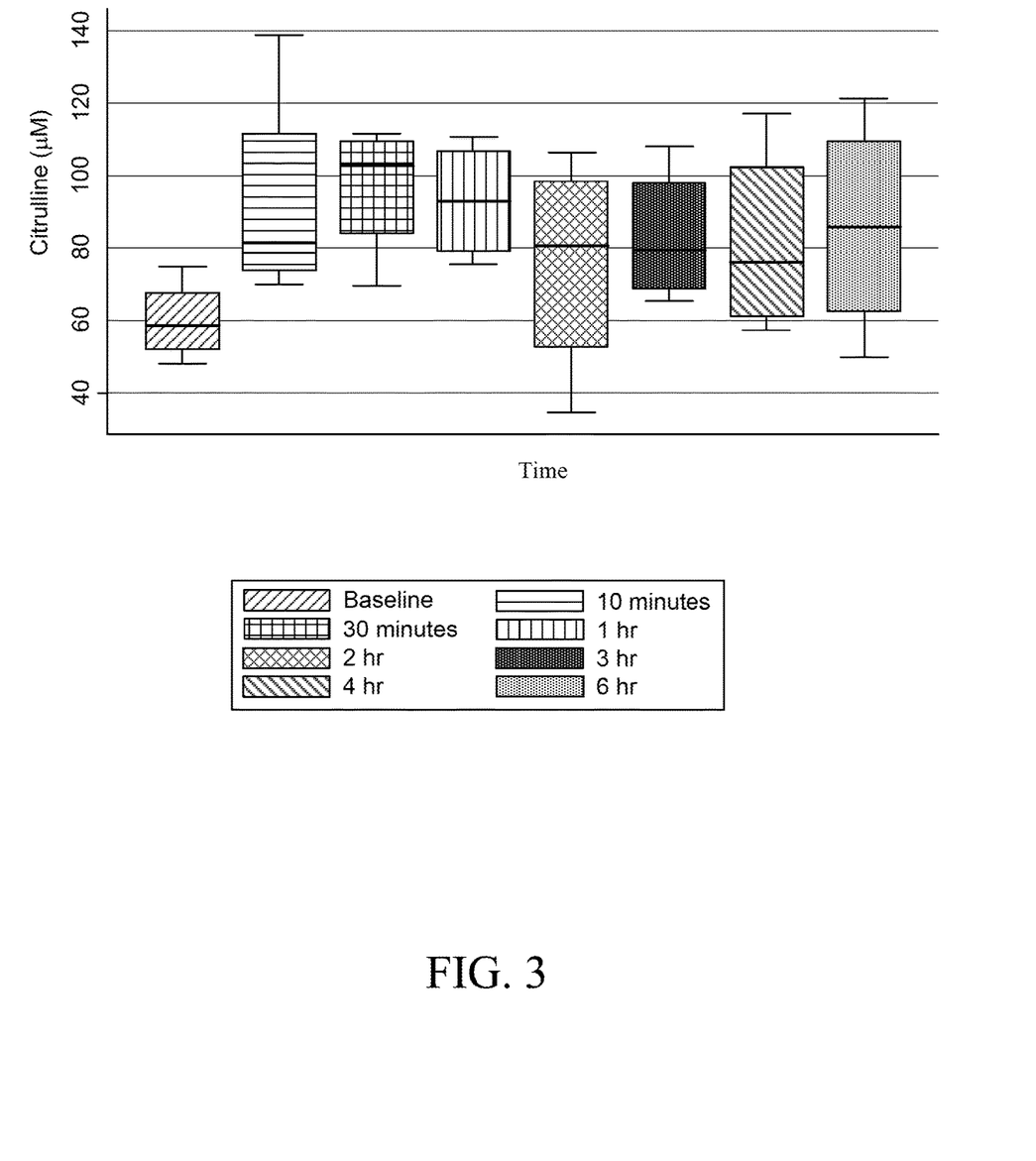
FIG. 3 depicts plasma arginine levels in Patients 1-4 over 6 hours following a 20 mg/kg intravenous bolus of citrulline within 5 minutes.
Figure 4:
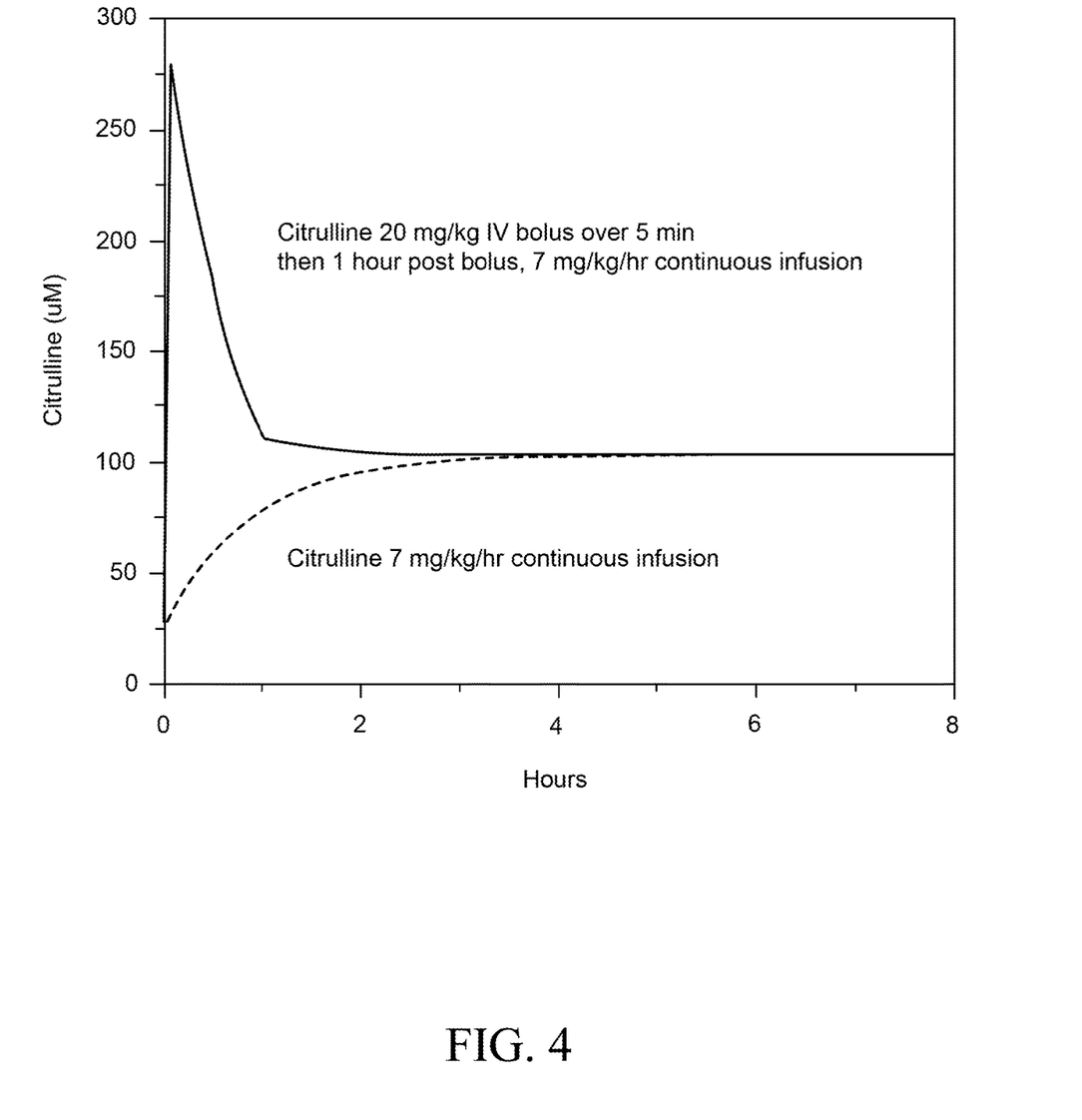
FIG. 4 depicts plasma citrulline levels over 6 hours following a 20 mg/kg intravenous bolus of citrulline over 5 minutes, then 1 hour post bolus, a 7 mg/kg/hr continuous infusion of citrulline.

Results: In the first cohort of four participants, the intravenous bolus infusion of 20 mg/kg of citrulline yielded a mean peak level of 259 µmol/L and trough level in the range of 20-40 µmol/L 4 hours after the infusion. FIG. 2. All subjects had a significant rise in their arginine level within one hour of receiving the bolus intravenous citrulline (mean increment of 182%). FIG. 3. One subject transiently dropped the diastolic blood pressure by >20% within 30 minutes of study drug with no intervention needed. There were no other reported side effects. Further analysis using a simulated dosing scheme indicates that a 20 mg/kg bolus dose of intravenous citrulline followed by a continuous infusion of 7 mg/kg/hour is needed to maintain the target citrulline concentration. See FIG. 4.

TABLE 1

Pharmacokinetic parameters for individual patients

| Patient | Rapp mmol/hr/kg | Krem 1/hr | V L/kg | CL L/hr/kg |
|---|---|---|---|---|
| 1 | 12.9 | 1.01 | 0.70 | 0.70 |
| 2 | 8.3 | 1.34 | 0.38 | 0.51 |
| 3 | 14.0 | 0.89 | 0.46 | 0.41 |
| 4 | 9.3 | 1.01 | 0.46 | 0.46 |
| Average | 11.1 | 1.06 | 0.50 | 0.52 |
| SD | 2.8 | 0.19 | 0.14 | 0.13 |

Conclusion: Bolus intravenous citrulline is safe and well tolerated in patients with SCD but has a rapid clearance. Continuous dose intravenous citrulline in SCD, including its effect on NO production, appears useful in treating sickle cell pain crisis.

While the foregoing invention has been described in connection with this preferred embodiment, it is not to be limited thereby but is to be limited solely by the scope of the claims which follow.

What is claimed is:

1. A method of treating a complication resulting from one or more occlusions formed during sickle cell crisis, the method comprising intravenously administering a bolus of a composition to a patient suffering from sickle cell crisis, wherein the composition comprises an effective amount of citrulline to manage sickle cell crisis, wherein the sickle cell crisis comprises vaso-occlusive crisis, acute chest syndrome, sequestration crisis, or a combination thereof, and wherein the complication resulting from the one or more occlusions comprises restriction of blood flow to an organ.

2. The method of claim 1, wherein the sickle cell crisis is vaso-occlusive crisis.

3. The method of claim 1, wherein the organ includes a lung, a spleen, a penis, or a combination thereof.

4. The method of claim 1, wherein the effective amount of citrulline is 100-1,000 mg/kg.

5. The method of claim 1, wherein the effective amount of citrulline is 100-1,000 mg in dose unit form.

6. The method of claim 1, wherein the effective amount of citrulline is 10-300 mg/kg.

7. The method of claim 1, wherein the effective amount of citrulline is up to 300 mg/kg.

8. The method of claim 1, wherein the method comprises an intravenous bolus of is 5-50 mg/kg of citrulline.

9. The method claim 1, wherein the method comprises an intravenous bolus of is 20 mg/kg of citrulline over 1-60 minutes.

10. The method of claim 1, wherein the method comprises a second intravenous bolus of 5-50 mg/kg of citrulline over 1-10 minutes, said second intravenous bolus being administered an hour after the first intravenous bolus of citrulline.

11. The method of claim 1, wherein the method comprises a continuous infusion of citrulline at 1-10 mg/kg/hour.

12. The method of claim 11, wherein the continuous infusion is for 1-24 hours.

13. The method of claim 1, wherein the patient's plasma citrulline level is raised above 100 µmol/L.

14. The method of claim 1, wherein the patient's plasma citrulline level is raised for up to 48 hours.

15. The method of claim 1, wherein the patient's plasma citrulline level is maintained above 50 µmol/L.

16. The method of claim 1, wherein the patient's plasma citrulline level is maintained above 75 µmol/L.

17. The method of claim 1, wherein the patient's plasma citrulline level is maintained above 150 µmol/L.

18. The method of claim 1, wherein the sickle cell crisis is acute chest syndrome.

19. The method of claim 1, wherein the sickle cell crisis is sequestration crisis.

* * * * *